US008043534B2

(12) United States Patent
Dershem

(10) Patent No.: US 8,043,534 B2
(45) Date of Patent: Oct. 25, 2011

(54) MALEIMIDE COMPOSITIONS AND METHODS FOR USE THEREOF

(75) Inventor: Stephen Dershem, San Diego, CA (US)

(73) Assignee: Designer Molecules, Inc., San Diego, CA (US)

( * ) Notice: Subject to any disclaimer, the term of this patent is extended or adjusted under 35 U.S.C. 154(b) by 900 days.

(21) Appl. No.: 11/786,441

(22) Filed: Apr. 12, 2007

(65) Prior Publication Data

US 2008/0075965 A1  Mar. 27, 2008

(51) Int. Cl.
*H01B 1/20* (2006.01)
*C09K 3/00* (2006.01)
*C09J 4/00* (2006.01)
*C09J 4/02* (2006.01)
*C09J 201/00* (2006.01)
*B32B 27/28* (2006.01)
*C08L 35/06* (2006.01)
*C08F 265/10* (2006.01)

(52) U.S. Cl. ... 252/511; 252/500; 252/510; 252/183.11; 156/330.9; 156/331.1; 156/331.5; 428/500; 525/205; 525/282; 526/262; 524/548; 524/516; 524/850; 522/152; 522/167; 522/173; 548/521

(58) Field of Classification Search ............... 525/205, 525/282; 526/262; 548/521; 524/548, 516, 524/850; 522/152, 167, 173; 252/500, 510, 252/511, 183.11; 156/330.9, 331.1, 331.5; 428/500
See application file for complete search history.

(56) References Cited

U.S. PATENT DOCUMENTS

| | | | |
|---|---|---|---|
| 3,905,820 A | 9/1975 | Frass | |
| 4,075,167 A | 2/1978 | Takamizawa et al. | |
| 4,111,879 A | 9/1978 | Mori et al. | |
| 4,224,216 A | 9/1980 | Locatelli et al. | |
| 4,371,719 A * | 2/1983 | Zahir et al. | 568/723 |
| 4,705,716 A | 11/1987 | Tang | |
| 4,894,281 A | 1/1990 | Yagi et al. | |
| 4,968,738 A | 11/1990 | Dershem | |
| 5,003,017 A * | 3/1991 | Eisenbarth et al. | 526/262 |
| 5,013,804 A * | 5/1991 | Kramer | 526/262 |
| 5,045,127 A | 9/1991 | Dershem et al. | |
| 5,064,480 A | 11/1991 | Dershem et al. | |
| 5,086,139 A * | 2/1992 | Corley | 526/262 |
| 5,087,705 A | 2/1992 | Okada et al. | |
| 5,095,074 A * | 3/1992 | Chu et al. | 525/422 |
| 5,120,823 A * | 6/1992 | Boyd | 528/310 |
| 5,143,969 A * | 9/1992 | Reck et al. | 524/548 |
| 5,155,177 A | 10/1992 | Frihart | |
| 5,189,116 A * | 2/1993 | Boyd et al. | 525/423 |
| 5,229,485 A * | 7/1993 | Kramer et al. | 528/353 |
| 5,232,962 A | 8/1993 | Dershem et al. | |
| 5,266,610 A | 11/1993 | Malhotra et al. | |
| 5,284,959 A | 2/1994 | Marien et al. | |
| 5,306,333 A | 4/1994 | Dershem et al. | |
| 5,315,011 A | 5/1994 | Benicewicz et al. | |
| 5,358,992 A | 10/1994 | Dershem et al. | |
| 5,393,887 A | 2/1995 | Petit | |
| 5,403,389 A | 4/1995 | Dershem | |
| 5,412,053 A | 5/1995 | Lichtenhan et al. | |
| 5,447,988 A | 9/1995 | Dershem et al. | |
| 5,484,867 A | 1/1996 | Lichtenhan et al. | |
| 5,489,641 A | 2/1996 | Dershem | |
| 5,554,769 A | 9/1996 | Sheppard et al. | |
| 5,567,761 A | 10/1996 | Song | |
| 5,602,205 A | 2/1997 | Singh et al. | |
| 5,616,666 A * | 4/1997 | Morton et al. | 526/262 |
| 5,646,241 A | 7/1997 | Dershem et al. | |
| 5,714,086 A | 2/1998 | Osuna et al. | |
| 5,717,034 A | 2/1998 | Dershem et al. | |
| 5,718,941 A | 2/1998 | Dershem et al. | |
| 5,753,748 A | 5/1998 | Dershem et al. | |
| 5,760,165 A | 6/1998 | Dao et al. | |
| 5,770,681 A * | 6/1998 | Corley | 528/322 |
| 5,861,111 A | 1/1999 | Dershem et al. | |
| 5,969,036 A | 10/1999 | Dershem | |
| 5,973,166 A | 10/1999 | Mizori et al. | |
| 6,030,703 A * | 2/2000 | Fan et al. | 428/378 |
| 6,034,150 A | 3/2000 | Hoyle et al. | |
| 6,034,194 A | 3/2000 | Dershem et al. | |
| 6,034,195 A | 3/2000 | Dershem et al. | |
| 6,063,828 A | 5/2000 | Ma et al. | |
| 6,087,447 A | 7/2000 | Stevens et al. | |
| 6,121,358 A | 9/2000 | Dershem et al. | |

(Continued)

FOREIGN PATENT DOCUMENTS

CN           1187507 A          7/1998

(Continued)

OTHER PUBLICATIONS

"Heat-proof photosensitive resiu composite—composed of pgfo. organpjsilsesquioxane and photosensitisiog agcut", *Derwent-Acc-No. 1990-159265* Abstracted-Pub-No. JP 02099955A.
Adamson, "Review of CSP and Flip Chip Underfill Processes and When to Use the Right Dispensing Tools For Efficient Manufacturing", Paper Presented at *GlobalTRONICS Technology Conference*,Singapore 2002, 1-6.
Andersson et al., "Initiator-Free Photopolymerization of an Aliphatic Vinyl Ether-Maleimide Monomer", *J Coatings Tech* 69: 1997, 91-95.
Chen et al., "Interfacial Properties of Metal/Polyimide Layered Strucutres", In *Micro Electronic Packaging Technology—Materials and Processes* (Shieh ed; *ASM International*, Metals Park, Ohio) 1989, 345-350.
Grenier-Loustalot et al., "Monofunctional maleimide or acetylene tennlnated model compounds-I. Molten state homopolymerization reactivity and kinetics", *European Polymer Journal* 34: 1998, 1705-1714.

(Continued)

*Primary Examiner* — Joseph D Anthony
(74) *Attorney, Agent, or Firm* — The Law Office of Jane K. Babin, Professional Corporation; Jane K. Babin

(57) ABSTRACT

The invention is based on the discovery that compositions containing certain maleimide compounds and aromatic diene compounds are useful as thermosetting resins for the electronic packaging industry. The invention compositions described herein can be cured in a variety of ways, with or without a catalyst. In some embodiments, the well-known "ene" reaction can be used to cure the compositions described herein, and therefore no catalyst is required.

13 Claims, No Drawings

U.S. PATENT DOCUMENTS

| | | |
|---|---|---|
| 6,187,886 B1 | 2/2001 | Husson et al. |
| 6,211,320 B1 | 4/2001 | Dershem et al. |
| 6,214,516 B1 | 4/2001 | Watson et al. |
| 6,214,923 B1 | 4/2001 | Goto et al. |
| 6,265,530 B1 | 7/2001 | Herr et al. |
| 6,281,314 B1 | 8/2001 | Tong et al. |
| 6,300,456 B1 | 10/2001 | Musa |
| 6,316,566 B1 | 11/2001 | Ma et al. |
| 6,355,750 B1 | 3/2002 | Herr |
| 6,369,124 B1 | 4/2002 | Hoyle et al. |
| 6,423,780 B1 | 7/2002 | Dershem et al. |
| 6,429,281 B1 | 8/2002 | Dershem et al. |
| 6,437,080 B1 | 8/2002 | McGrail et al. |
| 6,514,664 B1 | 2/2003 | Touky et al. |
| 6,521,731 B2 | 2/2003 | Dershem et al. |
| 6,610,808 B2 | 8/2003 | De et al. |
| 6,620,946 B2 | 9/2003 | Dershem et al. |
| 6,699,929 B2 | 3/2004 | Musa et al. |
| 6,716,919 B2 | 4/2004 | Lichtenhan et al. |
| 6,730,763 B1 * | 5/2004 | Okazaki et al. ............... 526/262 |
| 6,743,852 B2 | 6/2004 | Dershem et al. |
| 6,750,301 B1 | 6/2004 | Bonneau et al. |
| 6,790,597 B2 | 9/2004 | Dershem |
| 6,825,245 B2 | 11/2004 | Dershem |
| 6,831,132 B2 | 12/2004 | Liu et al. |
| 6,852,814 B2 | 2/2005 | Dershem et al. |
| 6,855,745 B2 | 2/2005 | Hoyle et al. |
| 6,881,820 B1 | 4/2005 | Meador et al. |
| 6,908,957 B2 | 6/2005 | Musa et al. |
| 6,916,856 B2 | 7/2005 | Dershem |
| 6,946,523 B2 | 9/2005 | Dershem et al. |
| 6,960,636 B2 | 11/2005 | Dershem et al. |
| 6,963,001 B2 | 11/2005 | Dershem et al. |
| 7,102,015 B2 | 9/2006 | Dershem et al. |
| 7,119,160 B2 | 10/2006 | Kodama et al. |
| 7,157,587 B2 | 1/2007 | Mizori et al. |
| 7,176,044 B2 | 2/2007 | Forray et al. |
| 7,199,249 B2 | 4/2007 | Liu et al. |
| 7,208,566 B2 | 4/2007 | Mizori et al. |
| 7,285,613 B2 | 10/2007 | Dershem et al. |
| 7,309,724 B2 | 12/2007 | Dershem et al. |
| 7,326,754 B2 | 2/2008 | Nikolic et al. |
| 7,517,925 B2 | 4/2009 | Dershem et al. |
| 7,678,879 B2 | 3/2010 | Dershem |
| 2002/0002238 A1 | 1/2002 | Laplante et al. |
| 2002/0010281 A1 | 1/2002 | Musa et al. |
| 2002/0062923 A1 | 5/2002 | Forray |
| 2002/0099168 A1 | 7/2002 | Dershem et al. |
| 2002/0188137 A1 | 12/2002 | Dershem et al. |
| 2002/0193541 A1 | 12/2002 | Dershem et al. |
| 2002/0198356 A1 | 12/2002 | Dershem et al. |
| 2003/0008992 A1 | 1/2003 | Dershem et al. |
| 2003/0055121 A1 | 3/2003 | Dershem et al. |
| 2003/0060531 A1 | 3/2003 | Dershem et al. |
| 2003/0068567 A1 | 4/2003 | Ono et al. |
| 2003/0083436 A1 | 5/2003 | Deitch |
| 2003/0087999 A1 | 5/2003 | Dershem et al. |
| 2003/0109666 A1 | 6/2003 | Dershem et al. |
| 2003/0125551 A1 | 7/2003 | Dershem et al. |
| 2003/0129438 A1 | 7/2003 | Becker et al. |
| 2003/0148226 A1 | 8/2003 | Kodama et al. |
| 2003/0166746 A1 | 9/2003 | Zhou et al. |
| 2003/0178138 A1 | 9/2003 | Tsukagoshi |
| 2003/0199638 A1 | 10/2003 | Liu et al. |
| 2003/0208016 A1 | 11/2003 | Dershem et al. |
| 2004/0006166 A1 | 1/2004 | Liu et al. |
| 2004/0019224 A1 | 1/2004 | Dershem et al. |
| 2004/0077798 A1 | 4/2004 | Dershem et al. |
| 2004/0082724 A1 | 4/2004 | Dershem et al. |
| 2004/0102566 A1 | 5/2004 | Forray et al. |
| 2004/0123948 A1 | 7/2004 | Dershem et al. |
| 2004/0225026 A1 | 11/2004 | Mizori et al. |
| 2004/0225045 A1 | 11/2004 | Forray |
| 2004/0225059 A1 | 11/2004 | Mizori et al. |
| 2005/0027082 A1 | 2/2005 | Narayan-Sarathy et al. |
| 2005/0107542 A1 | 5/2005 | Liu et al. |
| 2005/0136620 A1 | 6/2005 | Dershem et al. |
| 2005/0137277 A1 | 6/2005 | Dershem et al. |
| 2005/0137340 A1 | 6/2005 | Nikolic et al. |
| 2005/0267254 A1 | 12/2005 | Mizori et al. |
| 2005/0272888 A1 | 12/2005 | Dershem et al. |
| 2006/0009578 A1 | 1/2006 | Dershem |
| 2006/0030672 A1 | 2/2006 | Nikolic et al. |
| 2006/0063014 A1 | 3/2006 | Forray |
| 2006/0069232 A1 | 3/2006 | Dershem |
| 2006/0074196 A1 | 4/2006 | Lewandowski et al. |
| 2006/0089447 A1 | 4/2006 | Robertson et al. |
| 2006/0116476 A1 | 6/2006 | Cheng |
| 2006/0142517 A1 | 6/2006 | Dershem |
| 2007/0021533 A1 | 1/2007 | Yan et al. |
| 2007/0060683 A1 | 3/2007 | Musa et al. |
| 2007/0155869 A1 | 7/2007 | Dershem et al. |
| 2007/0205399 A1 | 9/2007 | Mizori |
| 2007/0299154 A1 | 12/2007 | Dershem et al. |
| 2008/0017308 A1 | 1/2008 | Dershem et al. |
| 2008/0075961 A1 | 3/2008 | Mizori |
| 2008/0075963 A1 | 3/2008 | Dershem |
| 2008/0075965 A1 | 3/2008 | Dershem |
| 2008/0103240 A1 | 5/2008 | Dershem |
| 2008/0142158 A1 | 6/2008 | Dershem |
| 2008/0146738 A1 | 6/2008 | Dershem |
| 2008/0160315 A1 | 7/2008 | Forray et al. |
| 2008/0191173 A1 | 8/2008 | Dershem et al. |
| 2008/0210375 A1 | 9/2008 | Dershem et al. |
| 2008/0251935 A1 | 10/2008 | Dershem |
| 2008/0257493 A1 | 10/2008 | Dershem |
| 2008/0262191 A1 | 10/2008 | Mizori |
| 2009/0020319 A1 * | 1/2009 | Yamada ........................ 174/255 |
| 2009/0061244 A1 | 3/2009 | Dershem |
| 2009/0215940 A1 | 8/2009 | Dershem |
| 2009/0288768 A1 | 11/2009 | Dershem |
| 2010/0041803 A1 | 2/2010 | Dershem |
| 2010/0041823 A1 | 2/2010 | Dershem |
| 2010/0041832 A1 | 2/2010 | Dershem |
| 2010/0041845 A1 | 2/2010 | Dershem et al. |
| 2010/0056671 A1 | 3/2010 | Dershem |
| 2010/0063184 A1 | 3/2010 | Dershem |

FOREIGN PATENT DOCUMENTS

| | | |
|---|---|---|
| EP | 0393713 | 6/1994 |
| EP | 1156034 | 11/2001 |
| EP | 1156036 | 11/2001 |
| JP | 2-99955 | 4/1990 |
| WO | WO-8604073 | 7/1986 |
| WO | WO-9406862 | 3/1994 |
| WO | WO-2004060330 | 7/2004 |
| WO | WO-2004099331 | 11/2004 |
| WO | WO-2005003231 | 1/2005 |
| WO | WO-2005121190 | 12/2005 |
| WO | WO-2007100329 | 9/2007 |
| WO | WO-2008077141 | 6/2008 |
| WO | WO-2008092168 | 7/2008 |
| WO | WO-2008124797 | 10/2008 |
| WO | WO-2008130894 | 10/2008 |
| WO | WO-2010019832 | 2/2010 |

OTHER PUBLICATIONS

Iizawa et al., "Regioselective reaction of oxiranes with S-Phenyl Thioesters catalyzed by quaternary onium salts or crown ether-metal salt compleses", *Bull Chem Soc Jpn*:62: 1989, 597-8.

Kohli et al., "Co-Polymerization of Maleimides and Vinyl Ethers: A Structural Study", *Macromolecules* 31: 1998, 5681-5689.

Krishnan et al., "Synthesis, Characterization, and Curing Kinetics of Novel Ladder-Like Polysilsesquioxanes Containing Side-Chain Maleimide Groups", *Journal of Polymer Science: Part A: Polymer Chemistry*. vol. 42: 2004, 4036-4016.

Pyriadi et al., "Cyclopolyimerization of N-allylimaleimide Polymer", *Polymer Preprints* 11: 1970, 60-65.

Tamaki et al., "Octa(aminophenyl)silsesquioxanc as a Nanoconstruction Site", *J. Am. Chem. Soc* , lot. 123, No. 49: 2001, 2416-12417.

Yamazaki et al., "Effect of N-substrtuents on polymerization reactivity of N-alkylitaconimides in radical polymerization", *European Polymer Journal* 33: 1997, 157-162.

* cited by examiner

MALEIMIDE COMPOSITIONS AND METHODS FOR USE THEREOF

FIELD OF THE INVENTION

The present invention relates to thermosetting adhesive compositions, methods of preparation and uses therefor. In particular, the present invention relates to thermosetting compositions containing a maleimides and aromatic dienes and/or polyenes.

BACKGROUND OF THE INVENTION

As the electronics industry advances, and production of light weight components increases, the development of new materials gives producers increased options for further improving the performance and ease of manufacture of such components. Adhesive compositions, particularly conductive adhesives, are used for a variety of purposes in the fabrication and assembly of semiconductor packages and microelectronic devices. The more prominent uses include bonding of electronic elements such as integrated circuit chips to lead frames or other substrates, and bonding of circuit packages or assemblies to printed wire boards.

Adhesives used in the electronic packaging industry typically contain a thermosetting resin combined with a filler and some type of curing initiator. These resins are primarily used in the electronics industry for the preparation of non-hermetic electronic packages. Adhesives useful for electronic packaging applications typically exhibit properties such as good mechanical strength, curing properties that do not affect the component or the carrier, and rheological properties compatible with application to microelectronic and semiconductor components. Examples of such packages are ball grid array (BGA) assemblies, super ball grid arrays, IC memory cards, chip carriers, hybrid circuits, chip-on-board, multi-chip modules, pin grid arrays, and the like.

For all these applications, the microelectronics industry continues to require new resins that are able to meet its varying demands. Accordingly, there is a need for the development of materials to address the requirements of this rapidly evolving industry.

An even broader need is for high performance matrix resins and adhesives for use in high performance applications. These applications include temperature resistant adhesives and components for use in automobile engine compartments, brake pads, aerospace re-entry vehicles, engine nacelles, kilns and boilers, etc. Other applications include those where a combination of high modulus and toughness are required such as in sail boat masts, golf clubs, tennis rackets, and airplane parts.

Bismaleimides have been an attractive class of thermoset resins because of their unique performance advantages. Bismaleimides can be cured via a variety of mechanisms. Homocures of bismaleimides produce polysuccinimide thermosets. These cross-linked polysuccinimides generally yield high glass transition temperature thermosets with excellent heat resistance and stiffness. However, the homo-cured bismaleimide resins are also noted for their extreme brittleness. One useful approach that has been used to improve the fracture toughness of bismaleimide thermosets has been to co-cure them with diene or polyene compounds via "ene" and/or Diels/Alder reactions. These co-cures can result in thermosets that retain the high thermal performance advantages of the original polysuccinimides while also providing a substantial improvement in fracture toughness.

The commercially available "ene" and/or Diels-Alder curatives for bismalemides include a variety of allyl and propenyl functional compounds. Examples of these compounds are shown below as C-1 through C-9. The most attractive curatives are those that can participate in both "ene" and Diels-Alder reactions (i.e. compounds C-1 through C-5). The C-6 through C-9 bismaleimide curatives, even though they generally co-cure with bismaleimides via the ene reaction alone, can be used at low levels as reactive diluents.

All of the commercial allyl and propenyl curatives react with bismalemides in one or more steps to yield thermoset resins. These reactions must generally be conducted at temperatures well above 200° C., and often over several hours. Furthermore, all of the dual reactive curatives (i.e. C-1 through C-5) are extremely viscous liquids or solids. The relatively low viscosity reactive diluents may be added, but their use is restricted by their inability to participate in both the "ene" and Diels-Alder reactions. Thus, the addition of significant levels of compounds C-6 through C-9 would degrade the performance of the final thermosets. There remains, therefore, a need for improved curatives for bismaleimide monomers.

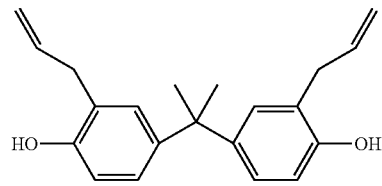

C-1

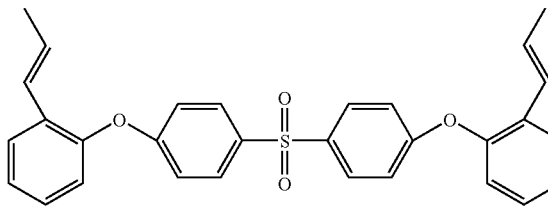

C-2

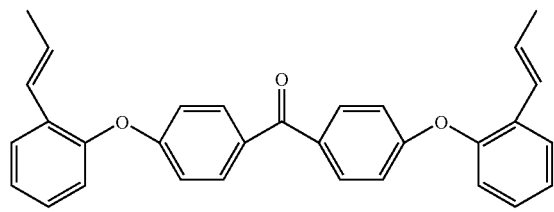

C-3

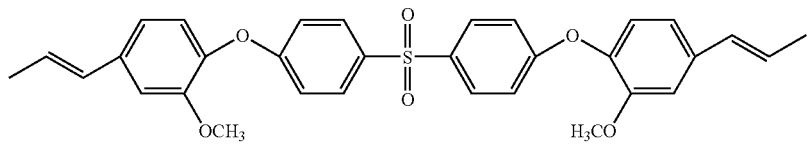

C-4

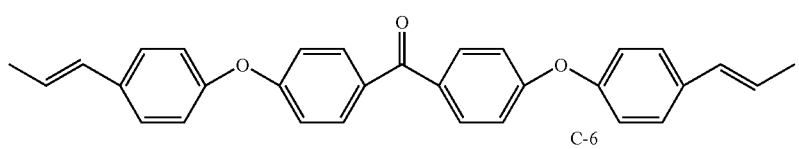

C-5

C-6

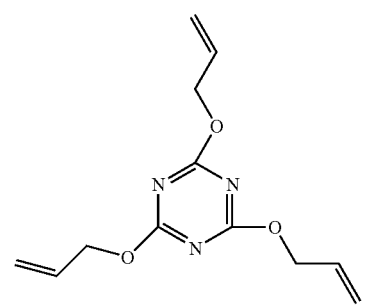

C-7

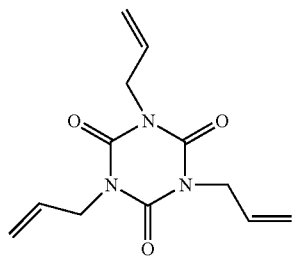

C-8

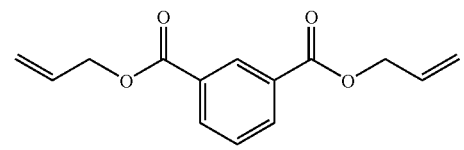

C-9

SUMMARY OF THE INVENTION

The invention is based on the discovery that compositions containing certain maleimide compounds and aromatic diene or polyene compounds are useful as thermosetting resins for the electronic packaging industry. The invention compositions described herein can be cured in a variety of ways with or without a catalyst. In some embodiments, the well-known "ene" and/or Diels-Alder reactions can be used to cure the compositions described herein.

The cured articles derived from the compositions described herein are notable for their excellent thermal and mechanical properties. These compositions polymerize via addition cure and thus generate no volatiles. The cure mechanisms also include ring formation, which results in low shrinkage during cure, low cure stress, and low coefficients of thermal expansion in the final thermoset. Furthermore, the cured articles of this invention are tough and resistant to brittle fracture.

One additional valuable aspect of the cure chemistry described in this invention is that it is insensitive to the presence of acidic fluxes. This is an important consideration since in some applications these materials are contemplated for use in no-flow underfill encapsulants. It is necessary to add solder fluxing compounds to insure a good bond between the solder bumps and the substrate they are being attached to. Other cure chemistries are incompatible with the acidic fluxes required for solder bump re-flow. Free-radical cures, for example, are poisoned by the presence of acidic species. Epoxy cures, while not poisoned by the acidic fluxes, react with these fluxes and thus demand higher levels of flux for effective re-flow. The insensitivity to acidic fluxes for the combination of compounds described herein is a significant advance for no-flow underfill materials chemistry.

An unexpected and very valuable aspect of this invention is based on the discovery that aromatic isopropenyl functional compounds can efficiently cure maleimide monomers. These cures can be accomplished in cure times measured in minutes and at temperatures below 200° C. This aspect of the invention significantly broadens the useful applications for non-radical, addition cure, maleimide thermoset chemistry.

Another useful class of maleimide curatives includes the aryl-methallyl compounds described herein. While not wishing to be bound by theory, it is believed that these compounds are more reactive than the traditional allyl maleimide curatives because the first stage, or ene, reaction results in a more highly substituted (and therefore more stable) double bond conjugated to the aromatic ring. The second stage, or Diels-Alder, reactions of these compounds are also more facile because double bonds substituted with electron donating groups enhance the rates of Diels-Alder addition reactions.

Another aspect of this invention is the discovery of a class of liquid and/or amorphous solid bismaleimide compounds that cure to high glass transition thermosets. Liquid bismaleimides have been described previously, however, these compounds have either been based on flexible (polysiloxane or long, branched aliphatic) spacer groups. The flexible residues drastically reduce the glass transition temperature and increase the coefficient of thermal expansion of the bismaleimides that contain them. The liquid and/or amorphous BMI monomers described herein derive their non-crystalline nature via the substantial absence of symmetry. They are generally viscous liquids or non-crystalline solids and are readily soluble in co-monomers. The necessary asymmetry to achieve this amorphous behavior can be achieved through the use of non-symmetric starting diamines or by the combination of methyl substituted and non-substituted maleimide end-groups. Practically speaking, it is often desirable to use a combination of both of these methods to obtain non-crystalline, high glass transition BMI monomers.

Another unique aspect of this invention is the discovery that polyacrylates (defined as monomers containing two or more acrylate functional groups per molecule) can also be used as curatives in the addition cure mechanisms for maleimide resins. Acrylates, themselves, are usually considered to be too weak as dieneophiles to participate in useful Diels-Alder cures. It has been found that polyacrylate monomers combined with mono, di- or polymaleimides along with isopropenyl functional aromatic compounds can be co-cured to give thermosets with very desirable properties.

In one embodiment of the invention, there are provided compositions including maleimide and an aromatic diene or polyene. In other embodiments, there are provided compositions including a liquid maleimide and an aromatic diene or polyene. In other embodiments, there are provided compositions including a maleimide, an aromatic diene or polyene, and a polyacrylate. In still other embodiments, there are provided compositions including a maleimide and an aromatic mono-ene. In other embodiments, there are provided compositions including a bismaleimide and an aromatic diene or polyene. In other embodiments, there are provided compositions including a liquid bismaleimide and an aromatic diene or polyene. In other embodiments, there are provided compositions including a bismaleimide, an aromatic diene or polyene, and a polyacrylate. In other embodiments, there are provided compositions including a polymaleimide, an aromatic diene or polyene and a polyacrylate. In another aspect of this invention there is provided a method to make isopropenyl terminated indane oligomers. In another aspect of the invention there are described several new liquid and/or amorphous, high $T_g$ bismaleimide resins.

In one embodiment of the invention, there are provided die-attach pastes including 2 weight percent to about 98 weight percent (wt %) of at least one invention composition, 0 to about 90 wt % of a filler, and 0.1 wt % to about 4 wt %, of at least one coupling agent.

In other embodiments, there are provided assemblies including a first article permanently adhered to a second article by a cured aliquot of the invention compositions set forth above.

In still another embodiment, there are provided methods for adhesively attaching a first article to a second article. Such methods can be performed, for example, by
(a) applying an aliquot of an invention adhesive composition to the first article,
(b) bringing the first and second article into intimate contact to form an assembly wherein the first article and the second article are separated only by the adhesive composition applied in (a), and thereafter,
(c) subjecting the assembly to conditions suitable to cure the adhesive composition.

In yet another embodiment, there are provided methods for adhesively attaching a semiconductor die to a substrate. Such methods can be performed, for example, by
(a) applying an invention die attach paste to the substrate and/or the semiconductor die,
(b) bringing the substrate and the die into intimate contact to form an assembly wherein the substrate and the die are separated only by the die-attach paste applied in (a), and thereafter,
(c) subjecting the assembly to conditions suitable to cure the die attach paste.

DETAILED DESCRIPTION OF THE INVENTION

The invention is based on the discovery that compositions containing certain maleimide compounds and aromatic diene and/or polyene compounds are useful as thermosetting resins for the electronic packaging industry. The invention compositions described herein can be cured in a variety of ways, with or without a catalyst. In some embodiments, the well-known "ene" and/or Diels-Alder reactions can be used to cure the compositions described herein, and therefore no catalyst is required.

As used herein, the term "aromatic diene" refers to any compound containing one or more aryl rings and two units of ethylenic unsaturation. "Ethylenic unsaturation" refers to a double bond between two carbon atoms, wherein the bond is not involved in aromatic delocalization of electron density. As used herein, the term aromatic polyene refers to any compound containing one or more aryl rings and more than two units of ethylenic unsaturation.

Typical aromatic dienes contemplated for use in the practice of the present invention include, but are not limited to, the isopropenyl compounds having the structure: and

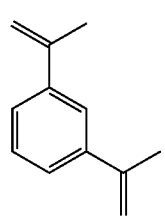

C-10

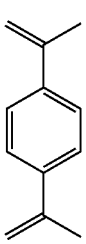

C-11

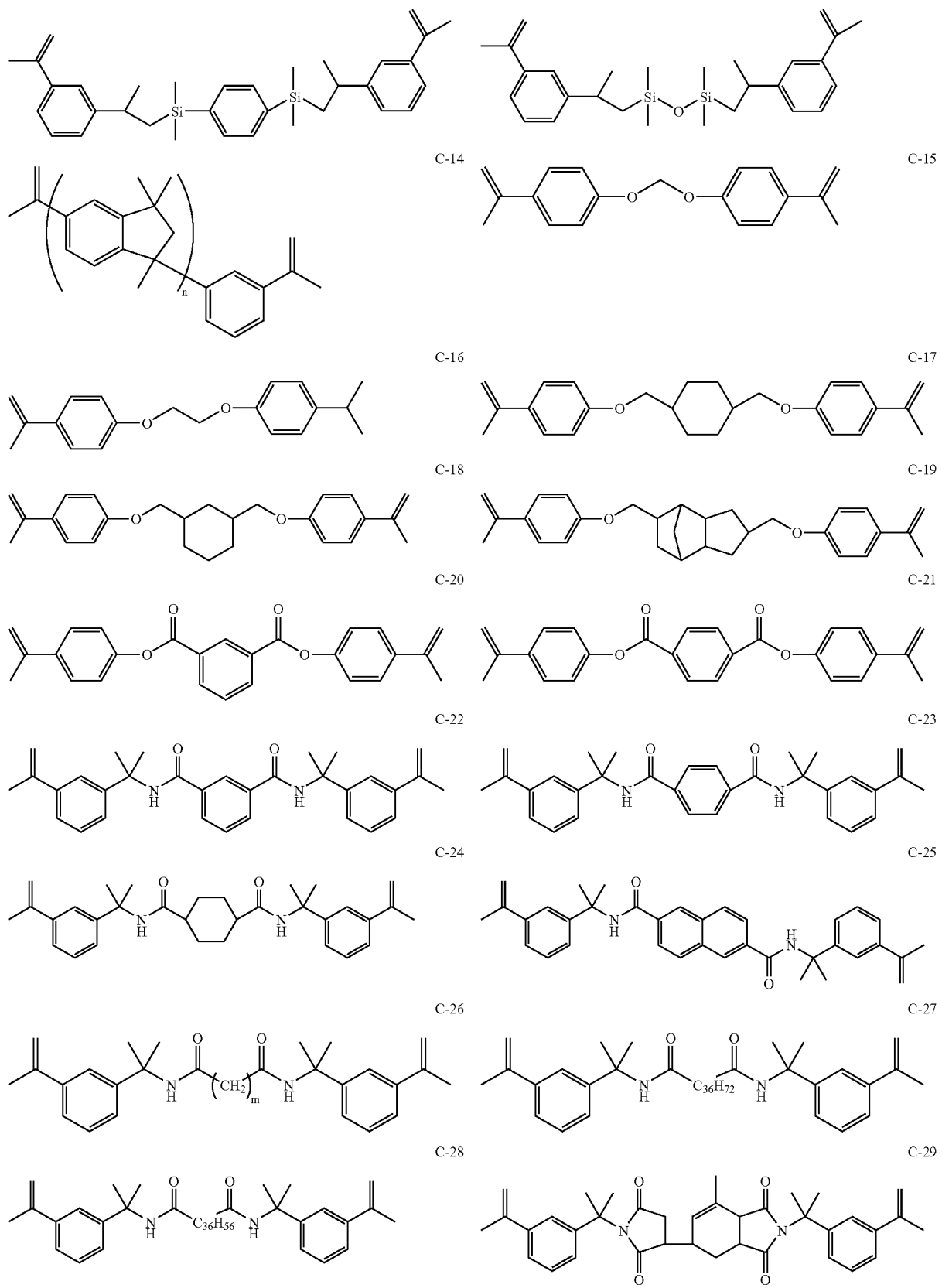

-continued

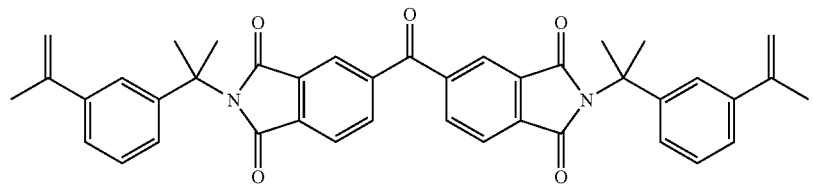
C-30

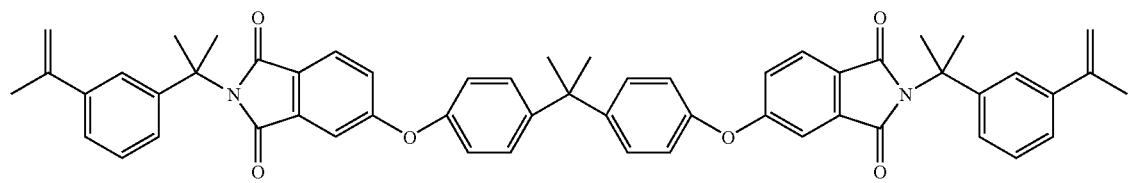
C-31

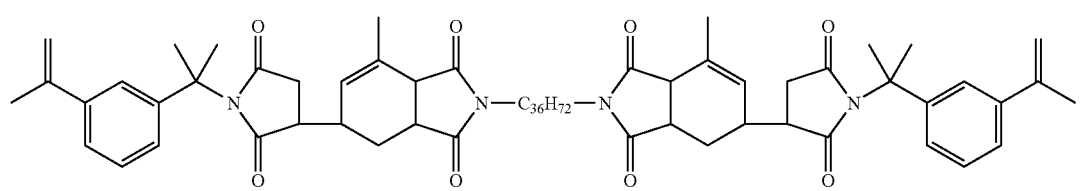
C-32

It is noteworthy that the compounds represented by "C-14" in the above curative structures can be obtained by the oligomerization of 1,3-diisopropenyl-benzene (DIIPB). Polymers of DIIPB have been previously described in U.S. Pat. No. 5,350,604. An outstanding property cited for those polymers was their extraordinarily low coefficient of thermal expansion, which was cited as 20 ppm/° C. between 25° and 250° C. We have found that liquid, low molecular weight, oligomers of DIIPB can be made using mild acid catalysts. These oligomers, furthermore, are soluble in the original DIIPB monomer itself, so their viscosity can be adjusted according to requirements of a particular application. These oligomers are, in some ways, ideal curatives for bismaleimide resins where the highly desirable properties of low thermal expansion and hydrophobicity are sought.

Additional aromatic dienes and contemplated for use in the practice of the present invention include, but are not limited to (and thus would include the corresponding propenyl and methylpropenyl isomers thereof), the allyl or methallyl compounds having the structure:

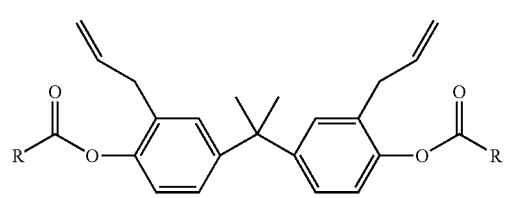
C-33

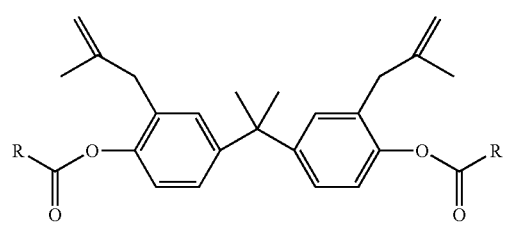
C-34

-continued

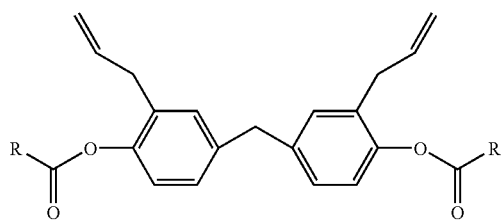
C-35

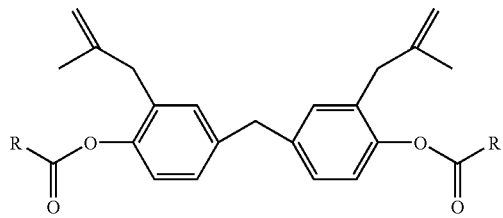
C-36

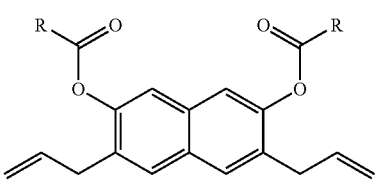
C-37

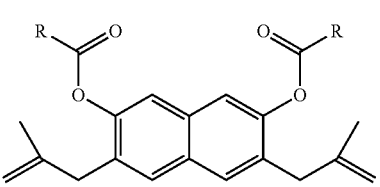
C-38

C-39
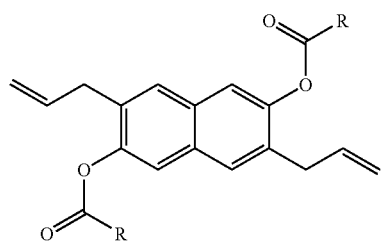
C-40
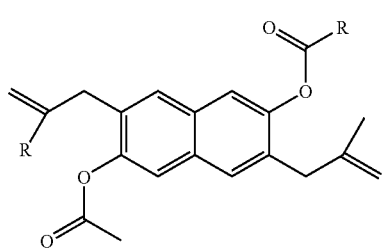
C-41
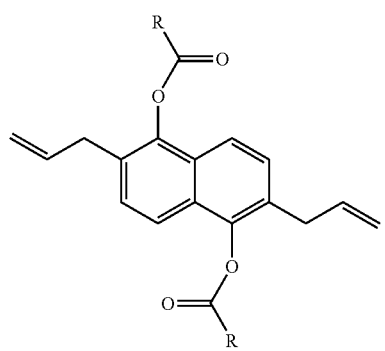
C-42
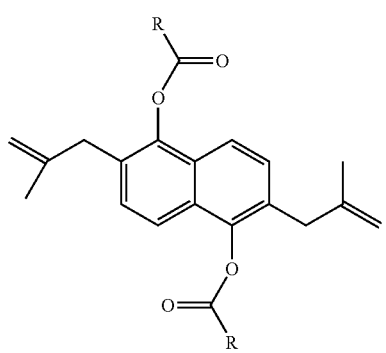
C-43
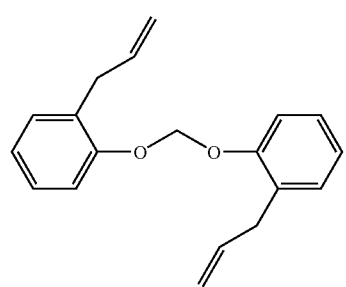
C-44
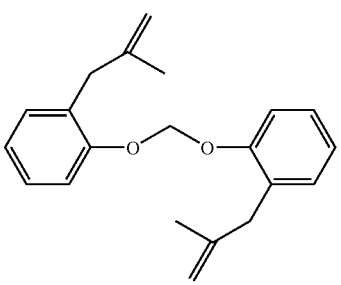
C-45
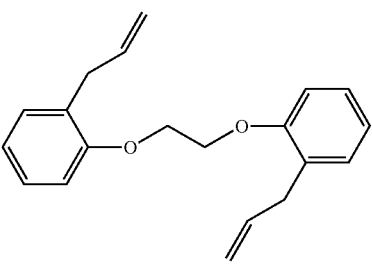
C-46
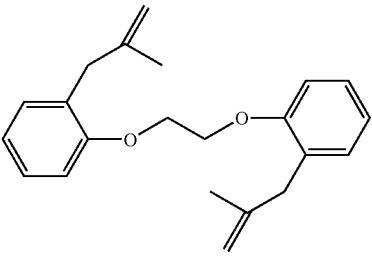
C-47
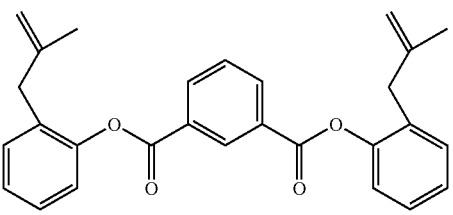
C-48
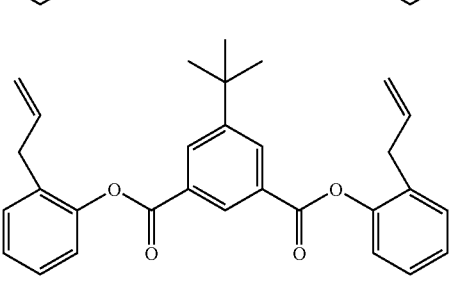
C-49

Wherein, "R" is methyl, ethyl, propyl, butyl, neobutyl, isopropyl, or isopropenyl. It should be noted that curative compounds C-33 through C-54 (as well as their propenyl and methylpropenyl isomers) are all relatively low viscosity liquids or low melting compounds.

Additional aromatic dienes and polyenes contemplated for use in the practice of the present invention include, but are not limited to (and thus would include the corresponding propenyl and methylpropenyl isomers thereof), the allyl or methallyl compounds having the structure:

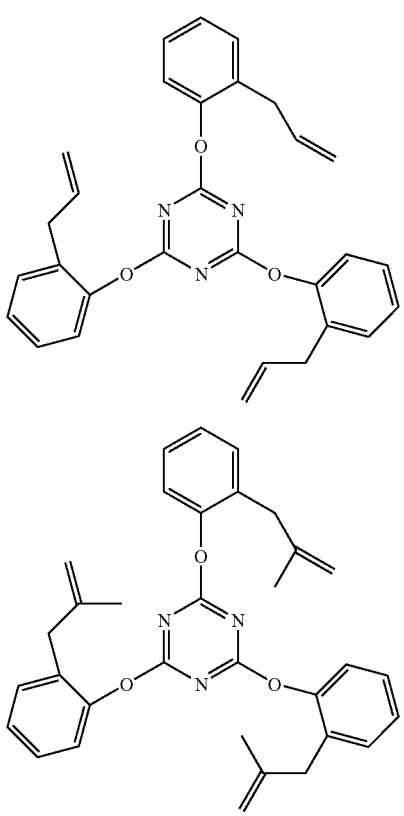

C-66

C-67

As used herein, "aliphatic" refers to any alkyl, alkenyl, cycloalkyl, or heterocyclic moiety.

As used herein, "alkyl" refers to straight or branched chain hydrocarbyl groups having from 1 up to about 100 carbon atoms. "Substituted alkyl" refers to alkyl moieties bearing substituents including alkyl, alkenyl, alkynyl, hydroxy, oxo, alkoxy, mercapto, cycloalkyl, substituted cycloalkyl, heterocyclic, substituted heterocyclic, aryl, substituted aryl, heteroaryl, substituted heteroaryl, aryloxy, substituted aryloxy, halogen, haloalkyl, cyano, nitro, nitrone, amino, amido, —C(O)H, —C(O)—O—, —C(O)—, —S—, —S(O)$_2$—, —OC(O)—O—, —NR—C(O)—, —NR—C(O)—NR—, —OC(O)—NR—, wherein R is H or lower alkyl, acyl, oxyacyl, carboxyl, carbamate, sulfonyl, sulfonamide, sulfuryl, and the like.

As used herein, "cycloalkyl" refers to cyclic ring-containing groups containing in the range of about 3 up to 8 carbon atoms, and "substituted cycloalkyl" refers to cycloalkyl groups further bearing one or more substituents as set forth above.

As used herein, "aryl" refers to aromatic groups having in the range of 6 up to 14 carbon atoms and "substituted aryl" refers to aryl groups further bearing one or more substituents as set forth above.

As used herein, "heterocyclic" refers to cyclic (i.e., ring-containing) groups containing one or more heteroatoms (e.g., N, O, S, or the like) as part of the ring structure, and having in the range of 3 up to 14 carbon atoms and "substituted heterocyclic" refers to heterocyclic groups further bearing one or more substituents as set forth above. The term heterocyclic is also intended to refer to heteroaromatic moieties.

As used herein, "alkenyl" refers to straight or branched chain hydrocarbyl groups having at least one carbon-carbon double bond, and having in the range of about 2 up to 100 carbon atoms, and "substituted alkenyl" refers to alkenyl groups further bearing one or more substituents as set forth above.

As used herein, "alkylene" refers to a divalent alkyl moiety, and "oxyalkylene" refers to an alkylene moiety containing at least one oxygen atom instead of a methylene (CH$_2$) unit. "Substituted alkylene" and "substituted oxyalkylene" refer to alkylene and oxyalkylene groups further bearing one or more substituents as set forth above.

As used herein, the term "maleimide" refers to the structure:

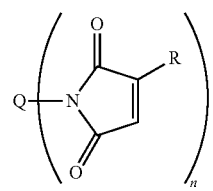

Wherein, "Q" is any of the hydrocarbon or substituted hydrocarbon residues noted above, "R" is hydrogen or methyl, and "n" is 1-6.

As used herein, the term "polyacrylate" refers to the structure:

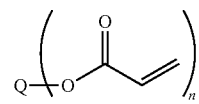

Wherein, "Q" is any of the hydrocarbon or substituted hydrocarbon residues noted above, and "n" is 1-6.

In one embodiment of the invention, the maleimide is a bismaleimide. In some embodiments, the maleimide is a liquid. In one embodiment, the maleimides have the structures:

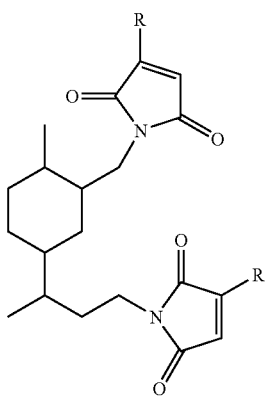

B-1

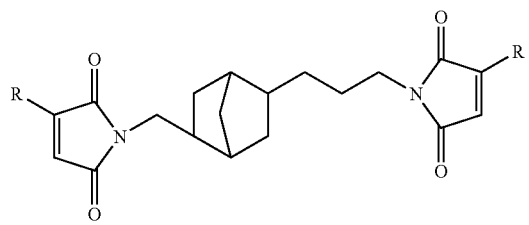

B-2

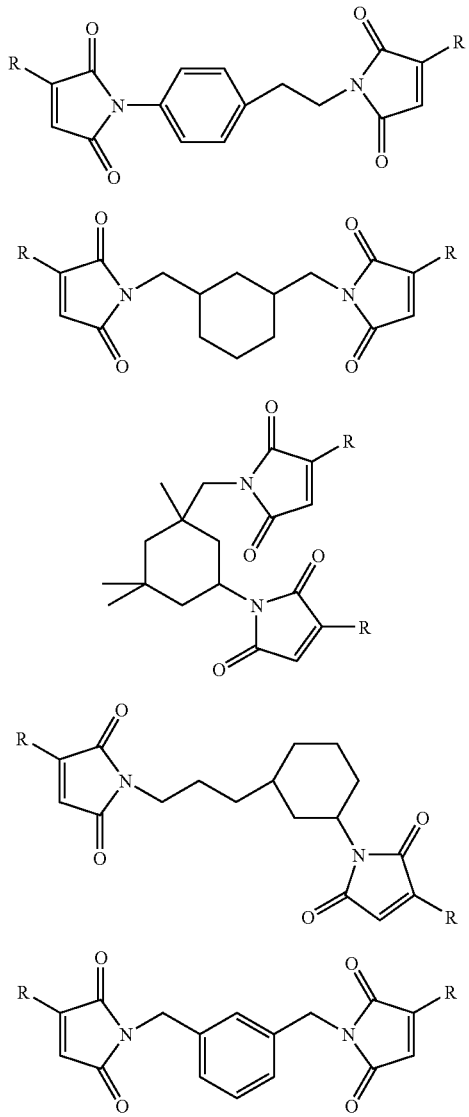

Where R = H or Me

In a further embodiment of the invention, there are provided die-attach pastes including the compositions of the invention. In some embodiments, the invention composition is present in the paste from 2 weight percent to about 98 weight percent (wt %). In other embodiments, there is at least additional compound that can co-cure with the maleimide and/or aromatic diene. The additional compound is typically present in the paste from 10 wt % to about 90 wt %. Such additional compounds include, for example, epoxies (phenolic, cresolic, aliphatic, cycloaliphatic and the like), cyanate esters, vinyl ethers, vinyl esters, vinyl acetates, olefins (such as polybutadine, poly(butadiene-co-acrylonitrile), polyisoprene, and the like), cyanoacrylates, styrenes, oxetanes, and the like, or combinations thereof.

In some embodiments, there is at least one curing initiator present in the composition from 0.1 wt % to about 5 wt %. In some embodiments, the curing initiator is a free-radical initiator. As used herein, the term "free radical initiator" refers to any chemical species which, upon exposure to sufficient energy (e.g., light, heat, or the like), decomposes into two parts which are uncharged, but which each possess at least one unpaired electron. Preferred free radical initiators contemplated for use in the practice of the present invention are compounds which decompose (i.e., have a half life in the range of about 10 hours) at temperatures in the range of about 70° C. up to 180° C. Exemplary free radical initiators contemplated for use in the practice of the present invention include peroxides (e.g., dicumyl peroxide, dibenzoyl peroxide, 2-butanone peroxide, tert-butyl perbenzoate, di-tert-butyl peroxide, 2,5-bis(tert-butylperoxy)-2,5-dimethylhexane, bis(tert-butyl peroxyisopropyl)benzene, and tert-butyl hydroperoxide), and the like.

The term "free radical initiator" also includes photoinitiators. For example, for invention adhesive compositions that contain a photoinitiator, the curing process can be initiated by UV radiation. In one embodiment, the photoinitiator is present at a concentration of 0.1 wt % to 5 wt % based on the total weight of the organic compounds in the composition (excluding any filler). In a one embodiment, the photoinitiator comprises 0.1 wt % to 3.0 wt %, based on the total weight of the organic compounds in the composition. Photoinitiators include benzoin derivatives, benzilketals, α,α-dialkoxyacetophenones, α-hydroxyalkylphenones, α-aminoalkylphenones, acylphosphine oxides, titanocene compounds, combinations of benzophenones and amines or Michler's ketone, and the like.

In a further embodiment, there are provided die-attach pastes including 2 weight percent to about 98 weight percent (wt %) of at least one invention composition, 0 to about 90 wt % of a filler, and 0.1 wt % to about 4 wt %, of at least one coupling agent.

The die-attach pastes described herein may further contain additional compounds that can co-cure with the maleimide and/or aromatic diene. Such compounds include, for example, epoxies (phenolic, cresolic, aliphatic, cycloaliphatic and the like), cyanate esters, vinyl ethers, vinyl esters, vinyl acetates, olefins (such as polybutadine, poly(butadiene-co-acrylonitrile), polyisoprene, and the like), cyanoacrylates, styrenes, oxetanes, and the like, or combinations thereof.

Fillers contemplated for use in the practice of the present invention can be non-conductive, or electrically conductive and/or thermally conductive. In addition, the fillers may act to modify the rheology of the resulting composition. Examples of suitable non-conductive fillers include silica, magnesium silicate, and calcium carbonate. Examples of suitable electrically conductive fillers which can be employed in the practice of the present invention include silver, nickel, copper, aluminum, palladium, gold, graphite, metal-coated graphite (e.g., nickel-coated graphite, copper-coated graphite, and the like), and the like. Examples of suitable thermally conductive fillers which can be employed in the practice of the present invention include graphite, aluminum nitride, silicon carbide, boron nitride, diamond dust, alumina, and the like. Compounds that act primarily to modify rheology include polysiloxanes (such as polydimethyl siloxanes) silica, fumed silica, alumina, titania, calcium carbonate, and the like.

As used herein, the term "coupling agent" refers to chemical species that are capable of bonding to a mineral surface and which also contain polymerizable reactive functional group(s) so as to enable interaction with the adhesive composition and/or die-attach paste. Coupling agents thus facilitate linkage of the die-attach paste to the substrate to which it is applied.

Exemplary coupling agents contemplated for use in the practice of the present invention include silicate esters, metal acrylate salts (e.g., aluminum methacrylate), titanates (e.g., titanium methacryloxyethylacetoacetate triisopropoxide), or compounds that contain a copolymerizable group and a chelating ligand (e.g., phosphine, mercaptan, acetoacetate, and the like). In some embodiments, the coupling agents contain both a co-polymerizable function (e.g., vinyl moiety, acrylate moiety, methacrylate moiety, and the like), as well as a silicate ester function. The silicate ester portion of the coupling agent is capable of condensing with metal hydroxides present on the mineral surface of substrate, while the co-polymerizable function is capable of co-polymerizing with the other reactive components of invention die-attach paste. In certain embodiments coupling agents contemplated for use in the practice of the invention are oligomeric silicate coupling agents such as poly(methoxyvinylsiloxane).

In some embodiments, both photoinitiation and thermal initiation may be desirable. For example, curing of a photoinitiator-containing adhesive can be started by UV irradiation, and in a later processing step, curing can be completed by the application of heat to accomplish a free-radical cure. Both UV and thermal initiators may therefore be added to the adhesive composition.

In general, the adhesive compositions and/or die-attach pastes will cure within a temperature range of 80-220° C., and curing will be effected within a length of time of less than 1 minute to 60 minutes. As will be understood by those skilled in the art, the time and temperature curing profile for each adhesive composition will vary, and different compositions can be designed to provide the curing profile that will be suited to the particular industrial manufacturing process.

In certain embodiments, the adhesive compositions and/or die-attach pastes may contain compounds that lend additional flexibility and toughness to the resultant cured adhesive. Such compounds may be any thermoset or thermoplastic material having a Tg of 50° C. or less, and typically will be a polymeric material characterized by free rotation about the chemical bonds, the presence of ether groups, and the absence of ring structures. Suitable such modifiers include polyacrylates, poly(butadiene), polyTHF (polymerized tetrahydrofuran, also known as poly(1,4-butanediol)), CTBN (carboxy-terminated butadiene-acrylonitrile) rubber, and polypropylene glycol. When present, toughening compounds may be in an amount up to about 15 percent by weight of the maleimide and other monofunctional vinyl compound.

Inhibitors for free-radial cure may also be added to the adhesive compositions and die-attach pastes described herein to extend the useful shelf life of compositions containing the functionalized urethane compounds described herein. Examples of these inhibitors include hindered phenols such as 2,6-di-tert-butyl-4-methylphenol; 2,6-di-tert-butyl-4-methoxyphenol; tert-butyl hydroquinone; tetrakis(methylene (3,5-di-tert-butyl-4-hydroxyhydrocinnamate))benzene; 2,2'-methylenebis(6-tert-butyl-p-cresol); and 1,3,5-trimethyl-2,4,6-tris(3',5'-di-tert-butyl-4-hydroxybenzyl)benzene. Other useful hydrogen-donating antioxidants include derivatives of p-phenylenediamine and diphenylamine. It is also well know in the art that hydrogen-donating antioxidants may be synergistically combined with quinones, and metal deactivators to make a very efficient inhibitor package. Examples of suitable quinones include benzoquinone, 2-tert butyl-1,4-benzoquinone; 2-phenyl-1,4-benzoquinone; naphthoquinone, and 2,5-dichloro-1,4-benzoquinone. Examples of metal deactivators include N,N'-bis(3,5-di-tert-butyl-4-hydroxyhydrocinnamoyl)hydrazine; oxalyl bis(benzylidenehydrazide); and N-phenyl-N'-(4-toluenesulfonyl)-p-phenylenediamine. Nitroxyl radical compounds such as TEMPO (2,2,6,6-tetramethyl-1-piperidnyloxy, free radical) are also effective as inhibitors at low concentrations. The total amount of antioxidant plus synergists typically falls in the range of 100 to 2000 ppm relative to the weight of total base resin. Other additives, such as adhesion promoters, in types and amounts known in the art, may also be added.

The adhesive compositions and die-attach pastes described herein will perform within the commercially acceptable range for die attach adhesives. Commercially acceptable values for die shear for the adhesives on a 80×80 $mil^2$ silicon die are in the range of greater than or equal to 1 kg at room temperature, and greater than or equal to 0.5 kg at 240° C.

In yet another embodiment of the invention, there are provided assemblies of components adhered together employing the above-described adhesive compositions and/or die attach pastes. Thus, for example, assemblies comprising a first article permanently adhered to a second article by a cured aliquot of the above-described adhesive composition are provided. Articles contemplated for assembly employing invention compositions include memory devices, ASIC devices, microprocessors, flash memory devices, and the like. Also contemplated are assemblies comprising a microelectronic device permanently adhered to a substrate by a cured aliquot of the above-described die attach paste. Microelectronic devices contemplated for use with invention die attach pastes include copper lead frames, Alloy 42 lead frames, silicon dice, gallium arsenide dice, germanium dice, and the like.

In other embodiments of the invention, there are provided methods for adhesively attaching a first article to a second article. Such methods can be performed, for example, by (a) applying an aliquot of an invention adhesive composition to the first article, (b) bringing the first and second article into intimate contact to form an assembly wherein the first article and the second article are separated only by the adhesive composition applied in (a), and thereafter, (c) subjecting the assembly to conditions suitable to cure the adhesive composition.

In still further embodiments, there are provided methods for adhesively attaching a semiconductor die to a substrate. Such methods can be performed, for example, by (a) applying an invention die attach paste to the substrate and/or the semiconductor die, (b) bringing the substrate and the die into intimate contact to form an assembly wherein the substrate and the die are separated only by the die-attach paste applied in (a), and thereafter, (c) subjecting the assembly to conditions suitable to cure the die attach paste.

Conditions suitable to cure invention die attach pastes include subjecting the above-described assembly to a temperature of less than about 200° C. for about 0.5 up to 2 minutes. This rapid, short duration heating can be accomplished in a variety of ways, e.g., with an in-line heated rail, a belt furnace, or the like. Optionally, the pastes can be oven cured at 150-220° C.

EXAMPLE 1

3,3'-diallyl-4,4'-diacetoxylbisphenol A (compound "C-33" where R=methyl): A 250 milliliter flask was charged with 30.84 grams (100 millimole) o,o'-diallylbisphenol A (Bixmax's "BX-ODBPA), 20.42 grams (200 millimole) acetic anhydride, and 0.5 grams DMAP catalyst. There was an immediate exotherm. The mixture was stirred at room temperature until the exotherm subsided and the flask was then placed on the rotovap and stirred at a bath temperature of 85° C. for an hour the residual acetic acid was then removed to yield 39.3 grams (100% of theory) of a light orange liquid.

The viscosity of this liquid was 2600 centipoise at 25° C. which was substantially lower than the viscosity of the o,o'-diallylbisphenol A starting material (15,400 centipoise at the same temperature). An FTIR spectrum of this compound confirmed the complete absence of phenolic hydroxyl functionality and the appearance of a prominent new absorption at 1759 wavenumbers.

EXAMPLE 2

Limonene bismaleimide (compound B-1, where both "R" groups=H): A one liter flask was charged with 400 milliliters toluene, 80 grams methane sulfonic acid, and 64 grams of triethylamine. The flask was equipped with a Dean-Stark trap and a condenser and the mixture was stirred at reflux for fifty minutes to remove residual water. Maleic anhydride (86.4 grams, 880 millimoles) along with 150 milligrams BHT was then dissolved into this mixture and 79.36 grams (400 millimoles) of limonene diamine was slowly added to the stirred solution over a period of forty-five minutes. There was an exotherm and a gummy slug of bismaleamic resin formed. The mixture was then refluxed for forty-five hours and 13.5 milliliters of water was collected in the trap. The reaction mixture was cooled to room temperature and 50 milliliters of deionized water was added. The upper toluene layer was decanted off and the residue was extracted six times with 100 milliliters of fresh toluene. The combined toluene fractions were allowed to settle overnight and this solution was then passed over 60 grams of silica gel. The toluene was removed to yield 100.4 grams (70% of theory) of a red, viscous, liquid. An FTIR was run on the product and it showed absorptions at 3461, 3100, 1690, 826, and 693 wavenumbers (all of which are characteristic for maleimides). A TGA run on this compound in the presence of two percent added dicumyl peroxide catalyst showed less than one percent weight loss at 300° C. and an onset for decomposition at 474° C. at a ramp rate of 10° C. per minute under an air purge.

EXAMPLE 3

Bismaleimide of vinylnorbornadiamine (compound B-2, where both "R" groups=H): A 500 milliliter flask was charged with 200 milliliters toluene, five grams methane sulfonic acid, and 40 milliliters NMP. Maleic anhydride (43.15 grams, 440 millimoles) was dissolved into this solution. Vinylnorbornadiamine (36.46 grams, 200 millimoles) was then slowly added over the course of fifteen minutes. A large gummy slug of the corresponding bismaleamic acid separated out, but stirring was not impeded. The flask was equipped with a Dean-Stark trap and condenser. The mixture was then stirred at reflux for twenty-four hours (the hazy mix became a homogeneous solution after about one milliliter of water had been removed). The mix was worked up in a fashion similar to Example 2 to give 49.2 grams (72% of theory) of a red, tacky, amorphous, semi-solid. The FTIR had absorptions at 3458, 3098, 1694, 825, and 693 wavenumbers. The TGA weight loss (air purge, 10° C./min. ramp) was less than one percent at 200° C. and the decomposition onset was 485° C.

EXAMPLE 4

Isophorone biscitraconimide (compound B-5 where both "R" groups=methyl): A 500 milliliter, single-neck flask was charged with 23.54 grams (210 millimoles) citraconic anhydride, and 150 milliliters toluene. This solution was stirred magnetically while 17.03 grams (100 millimoles) isophorone diamine was dripped in over a ten minute period. The mixture evolved heat. Stirring was continued for another ten minutes and then three grams methane sulfonic acid was added. The mix was refluxed for forty-two hours with an attached trap and condenser. The mix was then cooled and treated with ten grams sodium bicarbonate and two grams deionized water, followed by eight grams anhydrous magnesium sulfate. The solution was passed over twenty grams silica gel along with extra toluene rinses. The solvent was removed to yield 25.23 grams (70.4% of theory) of a clear, red, pliable, non-tacky solid at room temperature. This monomer was a viscous fluid at 70° C. It had FTIR absorbances at 3464, 3093, 1699, and 855 wavenumbers.

EXAMPLE 5

Vinylnorbornadiamine biscitraconimide (compound B-2 where both "R"=methyl): A 500 milliliter, single-neck flask was charged with 23.54 grams (210 millimoles) citraconic anhydride, 150 milliliters toluene, and 2.0 grams methane sulfonic acid. Vinylnorbornadiamine (18.23 grams, 100 millimoles) was added to the magnetically stirred solution over ten minutes. A trap and condenser were attached and the mix was refluxed for sixteen hours. The work-up was done in a fashion similar to Example 4 to give 31.1 grams (84% of theory) of a clear, red, tacky, very viscous liquid. The FTIR had absorptions at 3464, 3101, 1700, and 852 wavenumbers.

EXAMPLE 6

Bismaleimide of 1,3-xylene diamine (compound B-7 where both "R" groups=H): A 500 milliliter flask was charged with 200 milliliters toluene, 40 grams methane sulfonic acid, and 32 grams of triethylamine. The flask was equipped with a Dean-Stark trap and a condenser and the mixture was stirred at reflux for fifty minutes to remove residual water. Maleic anhydride (43.2 grams, 440 millimoles) along with 150 milligrams BHT was then dissolved into this mixture and 27.24 grams (200 millimoles) of 1,3-xylyene diamine was slowly added to the stirred solution over a period of fifteen minutes. This mix was then refluxed for twenty-seven hours. This mix was cooled to room temperature and the toluene phase was decanted off. The lower phase was extracted with seven 50 milliliter portions of fresh toluene. The combined toluene phase was settled overnight and then passed over thirty grams of silica gel. The solvent was removed to give 39.1 grams (66% of theory) of a white solid that was almost completely amorphous according to a DSC analysis. The compound had FTIR absorptions at 3453, 3095, 1698, 835, and 695 wavenumbers. The TGA weight loss for this compound was less than 0.5% at 300° C. and the decomposition onset was 478° C.

EXAMPLE 7

Oligomeric mixtures derived from 1,3-diisopropenylbenzene (compounds C-14): A 250 mL flask was charged with 30.0 g 1,3-diisopropenylbenzene, 120 mL heptane, and 5.0 g of dry Amberlyst 46 catalyst. This mix was refluxed for twenty-six hours and then the catalyst was filtered out and the heptane was removed to yield 27.6 g of a light-yellow, low viscosity liquid. A TGA was run on this material. It had 19.0% retained weight at 200° C., while a DIIPB control only had 1.8% residue at this same temperature. A second experiment was conducted where a vial was loaded with 0.5 g of zinc chloride and 2.0 g of DIIPB. This vial was heated overnight in an oven at 100° C. The next morning the vial had a clear solid fraction that was in contact with the zinc chloride catalyst, but most of the DIIPB had oligomerized to a clear, colorless syrup. A TGA run on this fraction had 80.5% retained weight at 200° C. Both of the above experiments demonstrated that it is possible to make oligomers of DIIPB and that these oligomers can be soluble in the original DIIPB monomer.

EXAMPLE 8

A mixture was made consisting of 82 parts by weight of the compound from Example 2 and 18 parts by weight DIIPB. This mix was cured at 130° C. for thirty minutes followed by one hour at 200° C. A TMA run on this solid showed a glass transition at 120.6° C. The CTE below the $T_g$ was 46.7 ppm/° C., and the CTE above the $T_g$ was 177 ppm/° C.

EXAMPLE 9

Another mix was made consisting of 75 parts by weight of the compound from Example 2 and 25 parts by weight DIIPB. This mix was cured for thirty minutes at 100° C., thirty minutes at 130° C., and forty-five minutes at 240° C. A TMA on this cured product had a remarkably high glass transition temperature of 261° C. The CTE below the $T_g$ was 53.5 ppm/° C. and above it was 154 ppm/° C.

EXAMPLE 10

A mixture was made consisting of 20.3 parts of the compound from Example 5, 17.3 parts DIIPB and 62.4 parts of a mixed acrylate/methacrylate of pentacyclopentadecane dimethanol. This mixture was cured at 200° C. and the $T_g$ was determined by TMA to be 102.4° C. The CTE below the $T_g$ temperature was 36.8 ppm/° C. and above it was 125.9 ppm/° C.

What is claimed is:

1. A composition comprising an adhesive material comprising:
   (a) a first compound, wherein the first compound is a maleimide, wherein the maleimide has the structure:

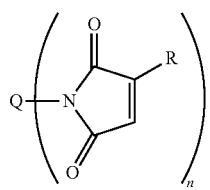

wherein:
Q is selected from the group consisting of a substituted or an unsubstituted alkyl, cycloalkyl, aryl, heterocylclic, alkenyl or alkylene,
R is selected from the group consisting of H and methyl, and
n is an integer having the value 1 or 3-6; and (b) a second compound, wherein the second compound is selected from the group consisting of:

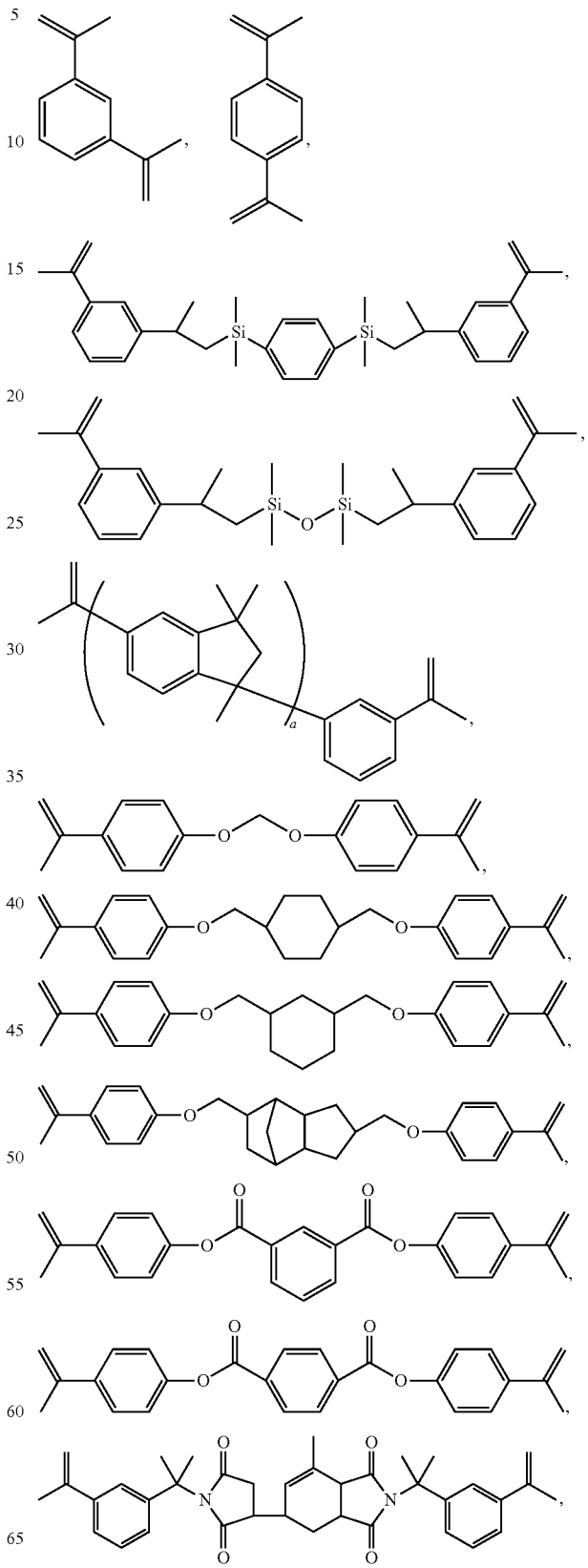

25
-continued
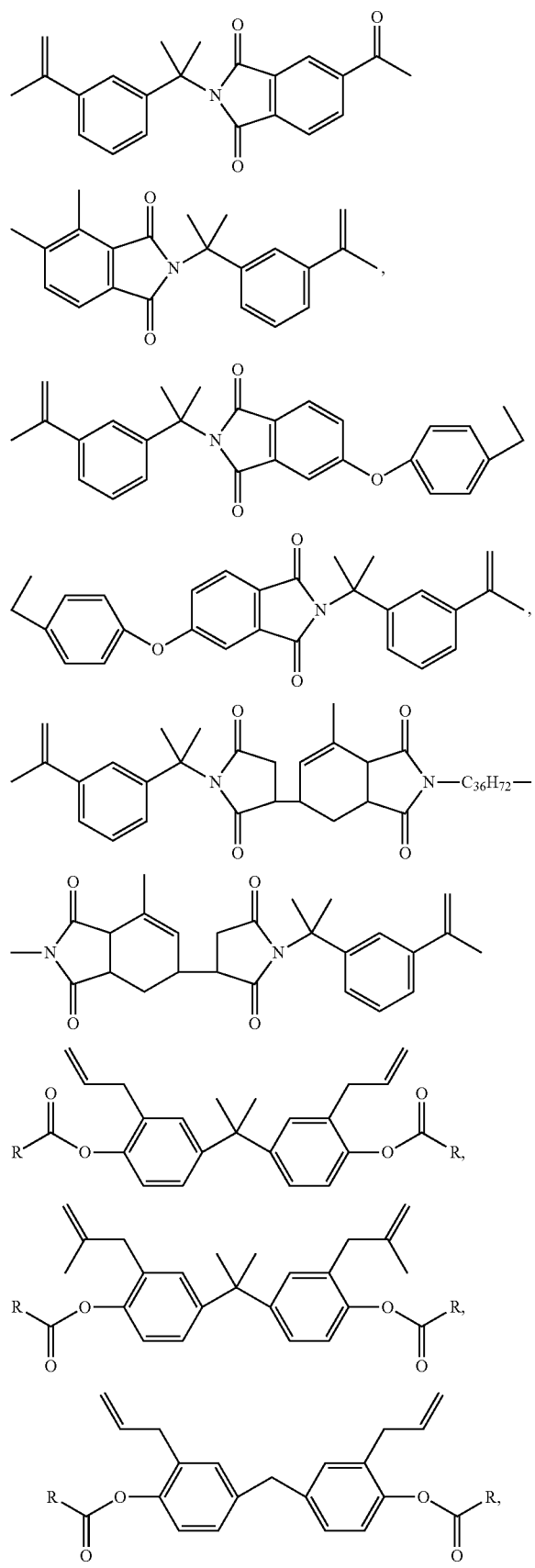
26
-continued
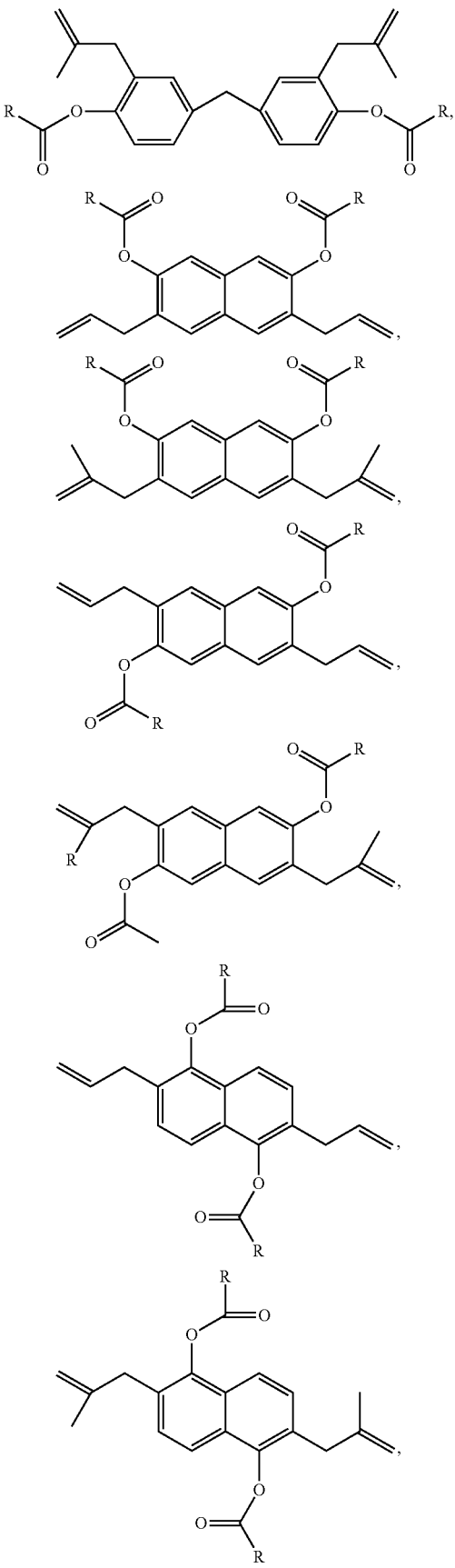

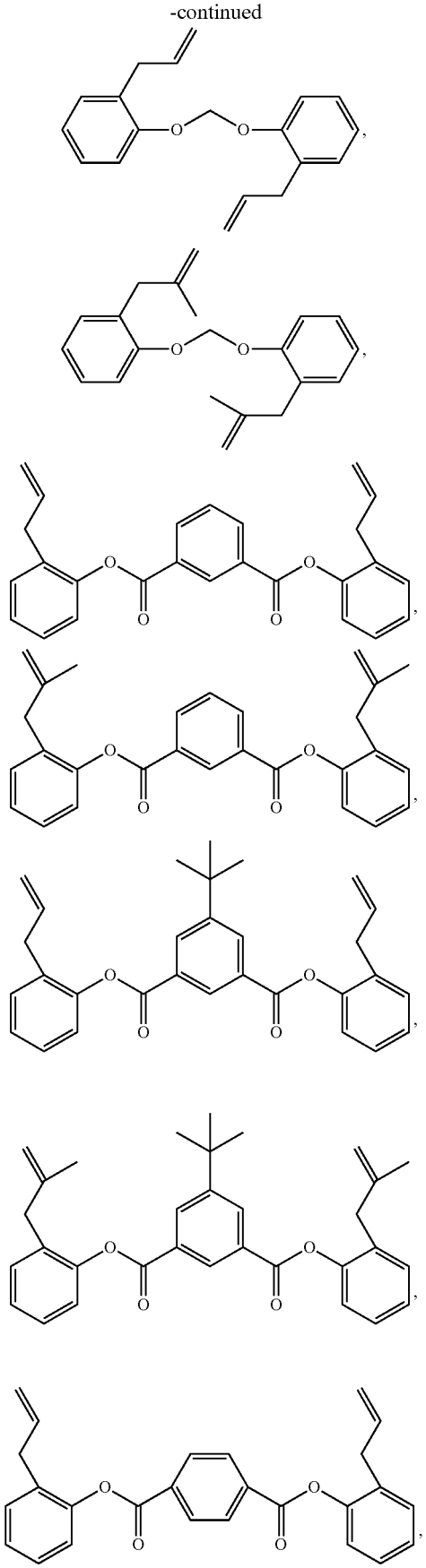
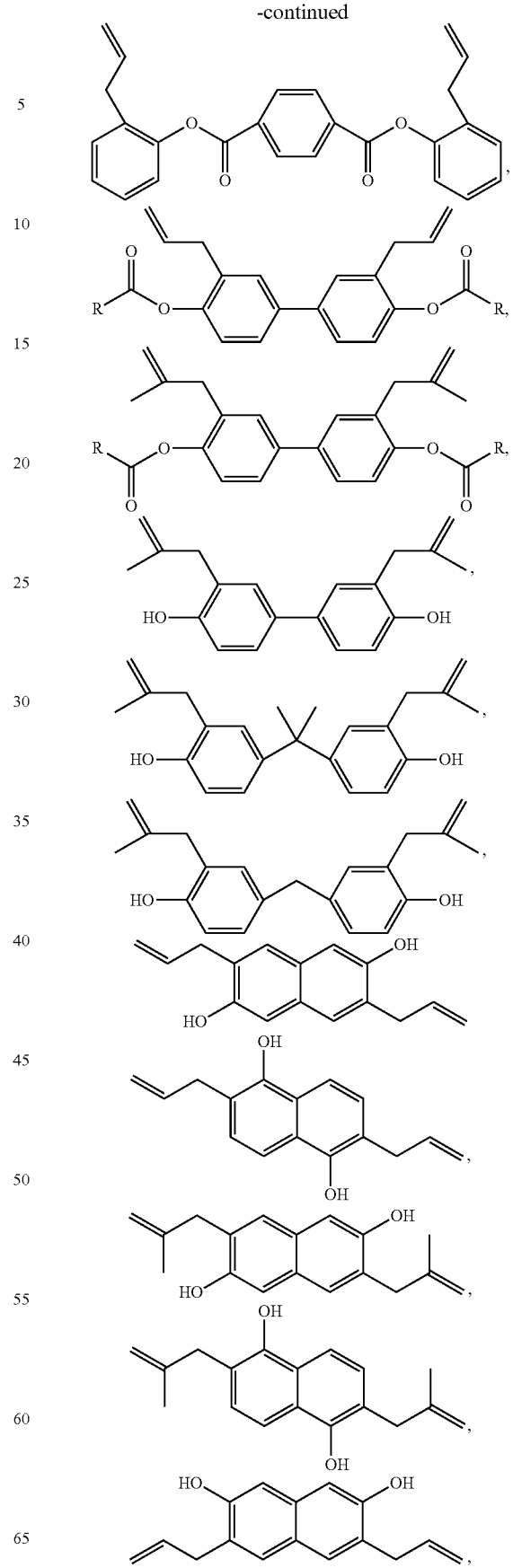

-continued

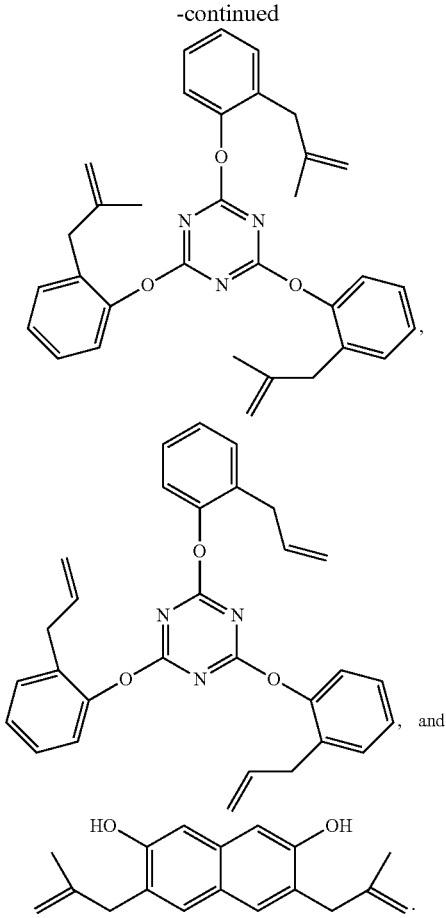

2. The composition of claim 1, wherein the maleimide is a liquid.

3. The composition of claim 1, wherein the second compound is an aromatic diene having the structure selected from the group consisting of

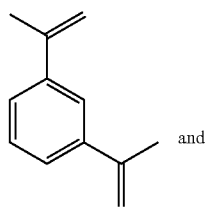 and

-continued

[structure: bis(2-allylphenyl) isophthalate]

4. The composition of claim 1, further comprising an additional compound selected from the group consisting of an acrylate, a methacrylate, a maleimide other than the first compound, a vinyl ether, a vinyl ester, a styrenic and an additional allyl functional compound.

5. The composition of claim 1, further comprising at least one curing initiator, reactive diluent, filler, or a combination thereof.

6. The composition of claim 5, wherein the filler is conductive.

7. The composition of claim 6, wherein the filler is thermally or electrically conductive.

8. The composition of claim 5, wherein the at least one curing initiator comprises 0.1 wt % to about 5 wt % based on total weight of the composition.

9. The composition of claim 5, wherein the curing initiator comprises a free-radical initiator or a photoinitiator.

10. The composition of claim 5 comprising:

a) 2 weight percent to about 98 weight percent (wt %) of the adhesive material;

b) 0 to about 90 wt % of the filler; and c) 0.1 wt % to about 4 wt %, of at least one coupling agent, wherein the composition is a die-attach paste.

11. The composition of claim 10, wherein the at least one curing initiator is present at 0.1 wt % to about 5 wt %.

12. The composition of claim 10, further comprising an additional compound selected from the group consisting of an acrylate, a methacrylate, a maleimide other than the first compound, a vinyl ether, a vinyl ester, a styrenic and an additional allyl functional compound.

13. The adhesive composition of claim 10, wherein the coupling agent is a silicate ester, a metal acrylate salt, or a titanate.

\* \* \* \* \*